United States Patent [19]

King et al.

[11] Patent Number: 5,294,434
[45] Date of Patent: Mar. 15, 1994

[54] ALOE VERA GEL TOOTHPASTE

[76] Inventors: Ronald M. King, 2623 Wesleyan Park Dr., Owensboro, Ky. 42301; Thomas F. Carroll, 2031 Barberry La., Bowling Green, Ky. 42104

[21] Appl. No.: 20,623

[22] Filed: Feb. 22, 1993

Related U.S. Application Data

[63] Continuation-in-part of Ser. No. 791,408, Nov. 14, 1991, abandoned, which is a continuation-in-part of Ser. No. 688,444, Apr. 22, 1991, abandoned.

[51] Int. Cl.$^5$ .......................... A61K 7/16; A61K 7/26; A61K 31/40; A61K 35/78
[52] U.S. Cl. ......................................... 424/58; 424/49; 424/195.1
[58] Field of Search ........................... 424/49.58, 195.1

[56] References Cited

U.S. PATENT DOCUMENTS

| | | | |
|---|---|---|---|
| 2,769,011 | 10/1956 | Hacker | 424/49 |
| 2,794,762 | 6/1957 | Westcott | 424/49 |
| 2,815,314 | 12/1957 | Hale | 424/58 |
| 3,137,632 | 6/1964 | Schiraldi | 424/49 |
| 3,892,853 | 1/1975 | Cobble | 424/58 |
| 4,069,311 | 1/1978 | Mannara I | 424/58 |
| 4,069,312 | 1/1978 | Mannara II | 424/58 |
| 4,814,160 | 3/1989 | Carter et al. | 424/58 |
| 4,853,213 | 8/1989 | Thame | 424/58 |

*Primary Examiner*—Shep K. Rose
*Attorney, Agent, or Firm*—Charles G. Lamb

[57] ABSTRACT

A toothpaste composition contains a dentifrice base which includes at least a detergent and an abrasive or polishing agent, and a mixture of aloe vera and chlorophyll. The toothpaste composition is useful in preventing gingivitis, controlling plaque and stimulating the growth of new tissue while reducing the hazards of bacterial contamination.

11 Claims, No Drawings

ALOE VERA GEL TOOTHPASTE

CROSS REFERENCE TO RELATED APPLICATIONS

This is a continuation-in-part application of pending patent application Ser. No. 07/791,408, filed Nov. 14, 1991, now abandoned, which is a continuation-in-part application of now abandoned patent application Ser. No. 07/688,444, filed Apr. 22, 1991.

BACKGROUND OF INVENTION AND DESCRIPTION OF PRIOR ART

Gingivitis, peridontal disease and diseases of the associated structures, i.e., interdental ligament and bone, alveolar bone and of tooth structure itself all have a common etiology; plaque. Plague in the oral cavity is ubiguitous and its control is critical not only to control inflammation, but also maintenance of healthy gums and fresh breath. Accordingly, this invention is directed to the control of plaque when used in a conscientiously applied program of oral hygiene care. It comprises a specific chlorophyll, aloe vera gel dentifrice in the form of a toothpaste.

It is known that chlorophyll possesses positive antibacterial actions and will stimulate growth of new tissue while reducing the hazards of bacterial contamination. The beneficial action of water soluble chlorophyll in oral sepsis has been reported by S. L. Goldberg, American Journal of Surgery, 62:117, (1943), wherein its curative action of pyorrhea, Vincent's angina, and gingivitis are discussed. U.S. Pat. No. 3,892,853 of Henry H. Cobble teaches the use of aloe vera gel by physicians and dentists in relieving pain and in promoting healing of topical and other lesions. Other toothpastes use aloe vera as an inhibiter and killer of bacteria which are known to cause plaque. This has also been noted to have a natural antibiotic action.

Also U.S. Pat. No. 4,748,022 of John A. Basciglio has introduced a composition and method for use in the treatment of pain and inflammation associated with lesions of skin and mucous membranes such as herpes simplex, herpes labialis, herpes progenitalis, chicken pox lesions, sensitivity of gingival tissue due to procedures for etching teeth with hydrochloride, swollen gums, cheilosis, oral traumatic injuries, aphthous ulcer by applying to the lesion an effective amount of topical composition comprising diphenhydramine HCL, lidocaine HCL, aloe vera gel, propilis in sufficient base to raise the pH to 8.9. Also pertinent is Japanese Patent No. 0116814 in which compositions are obtained by mixing 0.01 to 2 weight per cent of one menthol and or carevone with 0.01 to 1 weight per cent of aloe plant extract.

The chemistry of aloe vera gel has thus been investigated on and off for the past several decades, nevertheless, few studies have been well controlled and confirmed. Substances reported to occur in aloe vera gel include polysaccharides containing glucose, mannose, galactose, xylose, arabinose, tannins, steroids, organic acids, antibiotic principle(s), glucuronic acid, enzymes: oxidase, catalase, and amylase, trace sugars, calcium oxalate, a protein containing eighteen amino acids, "wound healing hormones", biogenic stimulators, saponins, vitamins, chloride, sulfate iron, calcium, copper, sodium, potassium, magnanese, zinc, etc.

It is commonly believed that the moisturizing emollient and healing properties of aloe vera gel are due to the polysaccharide present. The major polysaccharide present has been determined to be glucomannan. This glucomannan is a polysaccharide similar to guar and locust bean gums. Other polysaccharides containing galactose and uronic acids as well as pentoses are also present. It is believed probable that the gel's beneficial properties are not due to the polysaccharides alone, but rather from a synergistic effect of these compounds with other substances present in the gel. Still other research claims that a few of the basic components in aloe vera gel can also be found in DMSO, Dimethylsulfonic oxide, a wood pulp derivative which is currently used for treatment of rheumatoid arthritis and related complaints. Two constituents of both the gel and DSMO are: lignin, a wood-like pulp which has the remarkable ability to penetrate the human skin; and monosulfonic acid, an anthracene derivative found in the anthraquinone family of aloe vera and chemical chain derivative of DSMO. An enzyme derivative from amylase and a closely related variation of alpha amylase, is also thought to exist in both the gel and DSMO. Alpha amylase is well known for its penetrating, painkilling effectiveness in dealing with arthritis, bursitis and strain in muscle tissue. Some vitamins from the B-complex group i.e., B-1, niacinamide, B-2, B-6, ascorbic acid, vitamin C, and choline, the principal constituent of lecithin, have also been observed in aloe vera gel.

Photochemical reaction of chlorophylls per se include: a) reduction, b) oxidation, c) photosensitization, d) reversible photo-bleaching, e) sensitized oxidation reduction reactions not involving oxygen; insensitized oxidations involving oxygen. In 1920 the study of chlorophyll sensitized oxidation of various organic compounds by oxygen was begun by Noack, Meyer, Gaffron, and others. Sensitized reactions involving oxidants other than oxygen were first systemically studied by Bohi, who observed the bleaching of a number of azoyls and other oxygents in the presence of chlorophyll, phenylhydrazine and light. It has been noted that there is an energy transfer in vitro, chlorophyll involving a singlet excited chlorophyll molecule which may lose energy by radiationless transfer to a nearby molecule. Chlorophyll may also receive energy by transfer from some other exited molecule. An energy transfer from chlorophyll to chlorophyll is thus possible in concentrated solution. It has also been observed that a triplet state energy also occurs not only by the foster process, but also by an electron.

There has also been noted a cage effect, where the radicals formed and the reaction such as those previously mentioned are prevented from separating very far by the resistance in the medium. It was therefore concluded that there is a large probability that they will react to regenerate starting materials, this is the so-called "caged effect".

The existence of a long lived state of chlorophyll, intermediate energy between ground and first excited singlet states was originally postulated to explain the kinetics of photo-chemical reactions. In addition, there are rate limitations wherein less chlorophyll forms into a complex with a reagent in the dark. The rate constance for the bimolecular reactions are limited by the number of collisions per second between the reactive species.

Phosphorescence has also been studied, although its magnetic susceptibility has not been measured. The enhancement of phosphorescence by paramagnetic metal and copper pheophytins supports this belief. Energy transferred from a chlorophyll to an acceptor reaction has been demonstrated with reasonably certainty utilizing carotenoids. Unlike the one electron oxidation of chlorophyll, which usually reverses immediately upon cessation of illumination, reduction of chlorophyll leads to a stable non-radical product. Regarding energy requirements for the condition of the occurrence of primary reactions of chlorophyll: It was determined that for energy transfer reaction, the acceptor must have an excited electronic state of the proper multiplicity with energy less that that of the excited state of chlorophyll. More concerned, however, is the evidence of sensitized oxidations involving oxygen. The chlorophyll share with many other dyes the ability to sensitize the oxidation of organic substances by molecular oxygen. The only apparent requirement of a sensitizer is an existence of an excited state of sufficiently long lifetime to react with oxygen. Among the compound whose oxidation by chlorophyll, its derivatives, and other porpyhrins have been studied are benzidine, p-toluenediamine, aliphatic amines, phenylhydrazine, diphenylamine, and phenylendiamine, benzyl alcohol, pyruvic acid, ascorbic acid, cysteine, polyphenols, and cytachrome, ergosterol, serum protein, cseine, tyrosine, phenol, and uric acid which are oxidized to endoperoxides. This oxidation was found to have occurred in low $O_2$ pressure, even when the dye in substrate was absorbed into different silica gel particles. Another mechanism thus favored a primary photochemical reaction between the sensitizer chlorophyll and the reductant allythilurea. It is also argued that an electron transfer from a photoexcited dye to $O_2$ does the initial step in sensitizing oxidants as well as inflorescence quenching.

The complex chemical reactions of chlorophyll when mixed with aloe vera were carefully evaluated herein. In this connection, U.S. Pat. No. 3,878,197 of Ray H. Maret disclosed the process for extracting and stabilizing juice from leaves of the aloe vera plant. The gel was removed by trimming the rind and aloe layer from the leaf. The remaining gel digested under ultraviolet radiation at ambient temperature to produce biologically sterile and chemically stable extract of composition having characteristics similar to fresh aloe vera.

Moreover, in U.S. Pat. Nos. 4,853,213 and 4,952,392, Thame teaches an oral hygiene composition for reducing plaque and for the prevention and treatment of periodontal diseases wherein the composition comprises at least 0.03 per cent by weight of an extract of the perennial herb periwinkle. Aloe vera extract and chlorophyllin copper complex are referred to as being combinable with the periwinkle in a toothpaste composition.

SUMMARY OF INVENTION

In summarizing this new aloe vera gel-chlorophyll toothpaste invention, a number of outstanding features prevail. First, there was achieved an antibiotic and anti-inflammatory action of aloe vera gel; secondly, antibiotic and anti-inflammatory action of concentrated chlorophyll had developed; thirdly, there was the totally unexpected result of combining the chlorophyll-aloe vera gel composition, there envolving a considerable enhancement in the overall effectiveness in reducing gingival disease.

The present composition leads to a wide variety of enhancements related to the complexity in the mysterious nature of the aloe vera gel itself and to the presently discovered complexity and persistent energy exchange between the activated chlorophyll and the aloe vera gel, the apparent stabilization of the aloe vera gel when stabilized with an antioxidant. This is believed to be due to increased variables when the interactions of chlorophyll are intensified by the fact that conditions under which chlorophylls are photosensitized in aggregated states, are those wherein the pigment molecules are somewhat separated from each others micelles, emulsions, and wherein ultraviolet radiation is involved in both photosensitization and stabilization of aloe vera.

It has been found that in a proper ratio of aloe vera to chlorophyll in a commercially available dentifrice, gingivitis, periodontal disease and disease of the associated structures including interdental ligaments, bones, and tooth structures are controlled.

Particularly, the instant present invention is directed to a toothpaste composition including aloe vera and chlorophyll. More particularly, the present invention is directed to a toothpaste composition including a mixture of aloe vera and chlorophyll wherein the aloe vera and chlorophyll mixture is at least 1.5 percent by weight of the total composition mixture. Even more particularly, the present invention is directed to a toothpaste composition including aloe vera and chlorophyll wherein the ratio of aloe vera to chlorophyll is from about 10:1 to about 1000:1 parts by weight, and preferably of from about 10:1 to about 600:1 parts by weight.

DETAILED DESCRIPTION

There are commercially available a number of dentifrice compositions on the market for the use in the cleaning and protection of teeth as well as the gums, in some degree, of the user. All of these dentifrices include abrasive materials, compatible binders, thickners, wetting and foaming agents, and in many cases, a flavoring agent. In the description of the present invention, these compounds will be referred to as the "dentifrice base" or "inactive ingredients". The present invention is directed to the finding that commercially available dentifrices, when combined with the "active ingredients", aloe vera and chlorophyll, the removal of plaque, high response of healing of gum tissue, which in turn lowers gingivitis, periodontal disease and disease of the associated structures are enhanced.

The dentifrice base generally includes surfactants, abrasives or polishing agents, a humectant system, flavoring agents, as well as binders and buffering agents.

The components of the dentifrice base are fairly stable and non-reactive and as such do not require rigid environment, scientific or laboratory controls, in order to effect a homogeneous mixture. However, it should be noted that the mixture should be compounded in a sterile hood with the temperature between 60 degrees Fahrenheit, and 85 degrees Fahrenheit. By compounding the mixture at a temperature in the range of 60 degrees to 85 degrees Fahrenheit, a mixture that is stable as a gel with appropriate thickness or bulk to apply is obtained. In the mixing, the timing of the addition of a buffer, such as, calcium carbonate, and a thickener, such as, carrageenan is important. These two compounds should be added after all others are prepared and in solution and in so doing, both the viscosity and the pH can be controlled. Preferably, the pH of the mixture is held in the range of 6.5-7.9, by the calcium carbonate, in order to preserve the stabilized aloe vera gel and the chlorophyllin copper complex in solution prior to their activation in the more rigorous and acidic environment of the oral cavity.

Surfactants suitable for use in the present invention are any of the washing-active substances normally used in dentifrice bases which have a high foaming power and which are relatively stable to the salts responsible for the hardness of water. Preferred compounds are akaline metal salts of primary alkyl sulphates (fatty alcohol sulphates), of alkyl sulphonates, of condensation products of fatty acids and amino alkane sulphonic acids and/or amine oxides. In view of the high foaming power which is essential for a significant lighting in color of the foam, one preferred surfactant is a mixture of the sodium salt of alcohol sulfate and the sodium salt of myristic acid tauride.

Preferred abrasives and/or polishing agents include calcium phosphate, anahydrous NF which is a white odorless and tasteless power produced by various manufacturers through the addition of a phosphate mineral, e.g., apatite, and the subsequent participation of calcium phosphate after filtering and the addition of the proper quantity of calcium hydroxide. Calcium phosphate when ingested is an excellent source of exogenous calcium and a mild abrasive in the inventive mixture due to its load of resolibility in water and weak acids, less than 3% by weight. Other abrasive compounds that may be used include, but are not limited to dicalcium phosphate dihydrate, calcined alumina, calcium carbonate, hydrated alumina, sodium aluminosilicate, zirconimum silicate and the like.

A humectant system may also be included in the dentifrice base of the present invention. Generally a humectant system, which is usable in the present invention, will contain a major amount of sorbitol, multitole and mixtures thereof and optionally minor amounts of about 0 to 5% glycerine, and a high weight content of about 35 to 40% water. Other humectants such as polyethylene glycol and propylene glycol may partially replace the sorbitol and/or the glycerine humectant. Another preferred humectant is carrageenan NF 100%, which is valuable because of its long-termed stability and low reactivity with other chemicals leading to a long shelf life.

Binders and buffering agents may also be utilized in the present invention. A preferred binder and buffering agent is a calcium carbonate (precipitated calcium carbonate) NF, a fine white crystaline powder without odor or taste obtained through the double decomposition of calcium chloride and sodium carbonate in aqueous solution. However, other binders and buffering agents which are compatible with the other ingredients of the present invention may also be utilized without departing from the scope and spirit of the present invention.

Flavoring agents are also utilized in the present invention and includes those flavoring agents which are used in most commercially available dentifrices. These include, but are not limited to, oil of peppermint, oil of spearmint, oil of eucalyptus, cloves, menthol, anise, thyme, soluble saccharine and the like. Oil of wintergreen in a 25% solution is one preferred flavoring agent and is generally found as a natural extract of methyl solicylate obtained by maceration and subsequent distillation with steam from the leaves of *Gaultheria procumbens linnea*, Family Ericaceae. Oil of wintergreen has been reported to be useful also as a counter irritant when applied topically in low concentration of from 10 to 24% in an ointment solution.

The preferred aloe vera gel used in the present invention is a 100% stabilized, natural product obtained as a gel extract from the leaves of *Aloe barbadensis* and hybrids of the specis known as *Aloe afrincana* and *Aloe spicata*. The principle compounds are pentosides (5 carbon sugars) including aloin, beta-barbaloin and iso-barbaloin. The aloe vera gel relieves pain, reduces inflammation and tends to promote healing. The stabilized form provides the most useful shelf life and is readily available. Of the many aloe vera preparations available the 100% pure aloe vera gel is preferred in the inventive composition.

The chlorophyll used in the present invention is preferably a naturally occurring substance obtained from the green leaves of higher plants as a mixture of two closely related substances, chlorophyll a and chlorophyll b. Both chlorophylls occur as waxy blue-black crystals, and both occur as a magnesium complex salt.

The preferred chlorophyll is most commonly extracted on a commercial scale from dehydrated alfalfa leaf meal or broccoli leaf meal, both containing 0.2 to 0.4 per cent and 0.8 to 1.0 per cent of chlorophyll, respectively. And, the preferred chlorophyll derivative is copper-chlorophyll. Copper chlorophyll is generally obtained by the substitution of copper into the naturally occurring magnesium-chlorophyll salt via treatment with a mild or diluted acid containing copper. In the inventive mixture, chlorophyll as copper-chlorophyll was chosen due to the water solubility of the moiety and, more importantly, to the suspected bacteriostatic activity of either the copper-chlorophyll complex or of the activity of one or both of these parts when disassociated in solution in the complicated and diverse environment of the oral cavity. The present source of the copper chlorophyll compound is a 50 mg soft gelatin capsule (i.e., each capsule contains 50 mg of the chlorophyllin copper complex).

The preferred inventive composition is a gel for ease of use in the topical application to the teeth and oral soft tissues.

Pharmaceutical preservatives such as triethanolamine or tetra sodium ethylene diamine tetra acetic acid may be used. Critical to the success of the inventive composition is that the preservatives be compatible with the active ingredients. Moreover, the active ingredients may also be delivered to the field of treatment by way of a paste base as well as the described gel base as long as the pH of the resultant mixture is in the 6.5–7.9 range.

The following are examples given to explain in more detail the present invention. It is not intended that they be considered as limiting the scope of the invention, since they are illustrative only and by no means exhaustive.

In the following example the toothpaste composition included the dentifrice base as set forth in Table I below:

TABLE I

| | VOL. | WT. |
|---|---|---|
| Oil of wintergreen (25% solution | 3 ml | 90.0 mg. |
| Sorbitol NF (100% fine granules) | | 9.0 gms |
| Sodium Lauryl Sulfate NF (100% fine powder) | | 30.0 gms |
| Dicalcium Phosphate NF (100% very fine powder) | | 30.0 gms |
| Glycerine NF (100%) | 30 ml | 37.5 gms |
| Purified Water | 100 ml | 100.0 gms |
| Carrageenan (100% white-brown powder) | | 7.5 gms |
| Precipitated Calcium | 45.0–60.0 ml | 60.0 gms |

TABLE I-continued

| | VOL. | WT. |
|---|---|---|
| Carbonate (100%) | | |

EXAMPLE

A toothpaste composition was prepared which included in the composition the dentifrice base of Table I. To the toothpaste composition varying amounts of aloe vera and copper chlorophyll were added to determine the effect of various compositions on aloe vera and chlorophyll in the treatment of gum disease.

Clinical trials were performed on a group of thirty-four individuals wherein seven of the individuals identified in Table II as C-1 to C-5 were only given the dentifrice base to use as a toothpaste composition and twenty-seven other individuals were given the toothpaste composition including a specific aloe vera-copper chlorophyll mixture. In the Experimental group identified as E-1 to E-6, the ratio of aloe vera to copper chlorophyll was 200:1 parts by weight, in the group E-7 to E-11, the ratio of aloe vera to copper chlorophyll was 100:1; in the group of E-12 to E-16, the ratio of aloe vera to copper chlorophyll was 600:1; in the group of E-17 to E-19, the ratio of aloe vera to copper chlorophyll was 10:1; in the group of E-20 to E-23, the ratio of aloe vera to copper chlorophyll was 20:1; and, in the group of E-24 to E-27 the ratio of aloe vera to copper chlorophyll was 50:1.

Each of the individuals in the clinicals were examined prior to the clinical trials wherein the individuals in the examination were charted in order to determine the bleeding points in the gums (gingivitis). The participants were instructed to brush and floss routinely twice a day. The participants were then re-examined after from ten to fourteen days and the bleeding points were again charted. Bleeding point comparisons were made between the initial or start data (start) and the data obtained after using the provided dentifrices (finish).

The following is a table, Table II, which charts the differences using the dentifrice which was provided to the control group which did not have the aloe vera-chlorophyll mixture and the bleeding points of the experimental group which was provided with the aloe vera-chlorophyll mixture.

TABLE II

| | Start | Finish |
|---|---|---|
| Control - No Chlorophyll; No Aloe Vera Gel | | |
| C-1 | 122 | 100 |
| C-2 | 85 | 92 |
| C-3 | 101 | 78 |
| C-4 | 55 | 58 |
| C-5 | 51 | 43 |
| C-6 | 84 | 75 |
| C-7 | 103 | 96 |
| TRIAL A - Chlorophyll (50 mg/cc) 250 mg; Aloe Vera Gel (100%) 50 gms. | | |
| E-1 | 83 | 25 |
| E-2 | 102 | 16 |
| E-3 | 60 | 23 |
| E-4 | 85 | 25 |
| E-5 | 78 | 32 |
| E-6 | 74 | 29 |
| TRIAL B - Chlorophyll (50 mg/cc); Aloe Vera Gel (100%) 25 gms. | | |
| E-7 | 118 | 35 |
| E-8 | 102 | 25 |
| E-9 | 112 | 15 |
| E-10 | 85 | 37 |
| E-11 | 95 | 33 |
| TRIAL C - Chlorophyll (50 mg/cc) 250 mg; Aloe Vera Gel (100%) 75 gms. | | |
| E-12 | 105 | 27 |
| E-13 | 131 | 25 |
| E-14 | 110 | 32 |
| E-15 | 112 | 40 |
| E-16 | 106 | 31 |
| TRIAL D - Chlorophyll (50 mg/cc) 250 mg; Aloe Vera Gel (100%) 2.5 gms. | | |
| E-17 | 84 | 35 |
| E-18 | 113 | 32 |
| E-19 | 111 | 42 |
| TRIAL E - Chlorophyll (50 mg/cc) 250 mg; Aloe Vera Gel (100%) 5.0 gms. | | |
| E-20 | 71 | 30 |
| E-21 | 88 | 35 |
| E-22 | 101 | 40 |
| E-23 | 105 | 29 |
| TRIAL F - Chlorophyll (50 mg/cc) 250 mg; Aloe Vera Gel (100%) 12.5 gms. | | |
| E-24 | 122 | 41 |
| E-25 | 117 | 53 |
| E-26 | 112 | 26 |
| E-27 | 110 | 34 |

From these clinical trials, it is apparent that there was a substantial reduction in the bleeding points of the participants from start to finish while utilizing the toothpaste composition including the aloe vera-chlorophyll mixture, even as low as 1.5 per cent by weight of aloe vera in the total mixture and 0.09 per cent by weight of chlorophyll in the total mixture.

What is claimed is:

1. An additive for a dentifrice composition comprising a mixture of aloe vera and chlorophyll, the aloe vera-chlorophyll mixture being at least 1.5% by weight of the total composition mixture and the chlorophyll in the total composition mixture being at least 0.09% by weight.

2. The additive of claim 1 wherein the ratio of aloe vera to chlorophyll is from about 10:1 to about 1000:1 parts by weight.

3. The additive of claim 1 wherein the chlorophyll is copper chlorophyllin.

4. The additive of claim 1 wherein the aloe vera is in gel form.

5. The additive of claim 1 wherein the aloe vera to chlorophyll is from about 10:1 to about 600:1.

6. A toothpaste composition comprising a mixture of aloe vera and chlorophyll and a dentifrice base, said dentifrice base including a detergent and an abrasive, the aloe vera-chlorophyll mixture is being at least 1.5% by weight of the total composition and the chlorophyll in the total composition mixture being at least 0.09% by weight.

7. The toothpaste composition of claim 6 wherein the aloe vera is at least 1.5 per cent by weight of the total composition mixture.

8. The toothpaste composition of claim 6 wherein the chlorophyll is copper chlorophyllin.

9. The toothpaste composition of claim 6 wherein the aloe vera is in gel form.

10. The toothpaste composition of claim 6 wherein the dentifrice base further includes flavoring agents, a binder, a buffering agent and a humectant.

11. A method of making a toothpaste composition comprising the steps of:

a) making a first mix by mixing a detergent, an abrasive and water at a temperature of from about 60° F. to about 85° F;

b) making a second mix by adding a thickner and a buffering agent to said first mix while controlling the pH of a resulting mix to from about 6.5 to 7.9; and c) adding aloe vera-chlorophyll mix to said second mixture wherein the aloe vera-chlorophyll mix is at least 1.5% by weight of said second mixture and said chlorophyll is from at least 0.09% by weight of said second mixture.

* * * * *